(12) United States Patent
Griss et al.

(10) Patent No.: US 7,981,346 B2
(45) Date of Patent: Jul. 19, 2011

(54) MOLDED MICRO-NEEDLES

(75) Inventors: Patrick Griss, Rötelstrasse (CH); Göran Stemme, Ruddamsvägen (SE)

(73) Assignee: Bonsens AB, Stockholm (SE)

( * ) Notice: Subject to any disclaimer, the term of this patent is extended or adjusted under 35 U.S.C. 154(b) by 1046 days.

(21) Appl. No.: 11/661,113

(22) PCT Filed: Aug. 30, 2005

(86) PCT No.: PCT/SE2005/001260
§ 371 (c)(1),
(2), (4) Date: Jul. 6, 2007

(87) PCT Pub. No.: WO2006/025786
PCT Pub. Date: Mar. 9, 2006

(65) Prior Publication Data
US 2007/0255205 A1     Nov. 1, 2007

(30) Foreign Application Priority Data
Aug. 30, 2004  (SE) ...................................... 0402100

(51) Int. Cl.
*B28B 1/14*     (2006.01)
*B28B 1/48*     (2006.01)
*A61M 35/00*    (2006.01)
(52) U.S. Cl. .................... 264/299; 264/154; 604/289
(58) Field of Classification Search .................. 264/154, 264/299; 604/46, 47, 289, 304, 307
See application file for complete search history.

(56) References Cited

U.S. PATENT DOCUMENTS

| | | | |
|---|---|---|---|
| 4,838,877 A | 6/1989 | Massau | |
| 6,379,324 B1* | 4/2002 | Gartstein et al. | 604/22 |
| 6,451,240 B1* | 9/2002 | Sherman et al. | 264/504 |
| 6,629,949 B1 | 10/2003 | Douglas | |
| 6,881,203 B2* | 4/2005 | Delmore et al. | 604/272 |
| 6,899,838 B2* | 5/2005 | Lastovich | 264/102 |
| 7,578,954 B2* | 8/2009 | Gartstein et al. | 264/154 |
| 2002/0004643 A1 | 1/2002 | Carmel et al. | |
| 2002/0020688 A1* | 2/2002 | Sherman et al. | 216/2 |
| 2002/0082543 A1* | 6/2002 | Park et al. | 604/21 |
| 2002/0138049 A1* | 9/2002 | Allen et al. | 604/272 |
| 2002/2019375 | 12/2002 | CHO | |
| 2003/0009113 A1 | 1/2003 | Olson | |
| 2003/0045837 A1* | 3/2003 | Delmore et al. | 604/173 |

(Continued)

FOREIGN PATENT DOCUMENTS
WO    WO 00 35530    6/2000
WO    WO 03 015860   2/2003

*Primary Examiner* — Nicholas D Lucchesi
*Assistant Examiner* — Victoria P Campbell
(74) *Attorney, Agent, or Firm* — Young & Thompson

(57) ABSTRACT

Method of hollow micro-projections having side walls and at least one opening in a side wall, by a molding technique. The hollow micro-projections are defined by a first, negative mold defining the exterior shape of the micro-projections and a second, positive mold defining the hollow interior shape of the micro-projections. The method includes injecting a moldable material into the space between the two molds, in a state where they have been brought together. The positive and negative molds each have an essentially cylindrical geometry. In the process of bringing the molds together, the mold halves are laterally off-set with respect to each other, such that the distance between an inner wall of the negative mold and the positive mold in the area, ranges from zero to a finite distance. Micro-projections and arrays of micro-projections are also disclosed.

11 Claims, 8 Drawing Sheets

U.S. PATENT DOCUMENTS

| | | | |
|---|---|---|---|
| 2003/0093040 A1* | 5/2003 | Mikszta et al. | 604/289 |
| 2003/0135166 A1* | 7/2003 | Gonnelli | 604/264 |
| 2003/0135167 A1* | 7/2003 | Gonnelli | 604/272 |
| 2003/0199810 A1* | 10/2003 | Trautman et al. | 604/46 |
| 2004/0039343 A1* | 2/2004 | Eppstein et al. | 604/200 |
| 2004/0106904 A1* | 6/2004 | Gonnelli et al. | 604/173 |
| 2004/0265365 A1* | 12/2004 | Daddona et al. | 424/449 |
| 2005/0137531 A1* | 6/2005 | Prausnitz et al. | 604/173 |

* cited by examiner

MOLDED MICRO-NEEDLES

The present invention relates to a method of fabricating hollow micro projections comprising a sharp tip as well as at least one opening in the side surface of said projection. It also relates to the projections, in particular in the form of micro needles, suitable for a number of applications, such as micro injections of substances in the medical field.

BACKGROUND OF THE INVENTION

In applicants' own international patent application WO 03/015860 A1 ("Micro Needles and Method of Manufacture Thereof") there is disclosed a method of manufacturing hollow micro-projections having side openings. Such projections are suitable for use as micro needles for e.g. injection through the skin of medicaments.

The method disclosed in said WO publication is based on micro machining of e.g. silicon substrates.

In an article by A. E. Guber et al ("Polymer Micro Needles With Through-going Capillaries", in *Micro Total Analysis Systems* 2001, eds. Ramsey and van den Berg, pp 155-156), there is disclosed a method of making micro-needles by micro replicating. A first mold insert having a 1 mm deep conic hole, and a second mold insert, carrying a tin needle fitting in the mold are used. The first mold insert is made by a combination of micro machining and electroforming. The needle on the second mold insert is made by grinding tungsten carbide, and inserting the needle into a brass body. The product of the disclosed process is a conical projection (needle) with an inner lumen and an opening at the tip of the cone, the opening being made by laser drilling.

These prior art devices and methods, while contributing to the development of the technology, still suffer from some drawbacks. The device according to WO 03/015860 A1 requires bulk etching of material, which means that the cost of manufacture is affected by the use of excess material, i.e. large quantities of the bulk material must be removed to yield an array of microneedles. This may result in long fabrication and process times and thus in high cost.

The device disclosed by Gruber et al eliminates the use of excess material by using a molding technique, but instead require fairly complicated mold making technology, the opening requires an additional step (laser drilling), and above all, it dose not enable manufacture of side-opened needles.

In U.S. patent application Ser. No. 10/417,541 (US 2003/0208138 A1, published Nov. 6, 2003) there is disclosed a method of micro-replicating to provide micro-needles. However, the needles obtained are conical and have an opening at the apex of the cone, and are therefore unsuitable for certain applications.

SUMMARY OF THE INVENTION

Thus, the object of the present invention is to provide a method of manufacturing micro-needles overcoming the problem of using excess material and providing needles having openings in the sides thereof.

This object is achieved in accordance with the invention by the method as defined in claim 1.

BRIEF DESCRIPTION OF THE DRAWINGS

The invention will be describe below with reference to the drawings in which.

DETAILED DESCRIPTION OF THE INVENTION AND PREFERRED EMBODIMENTS THEREOF

Figure 1:
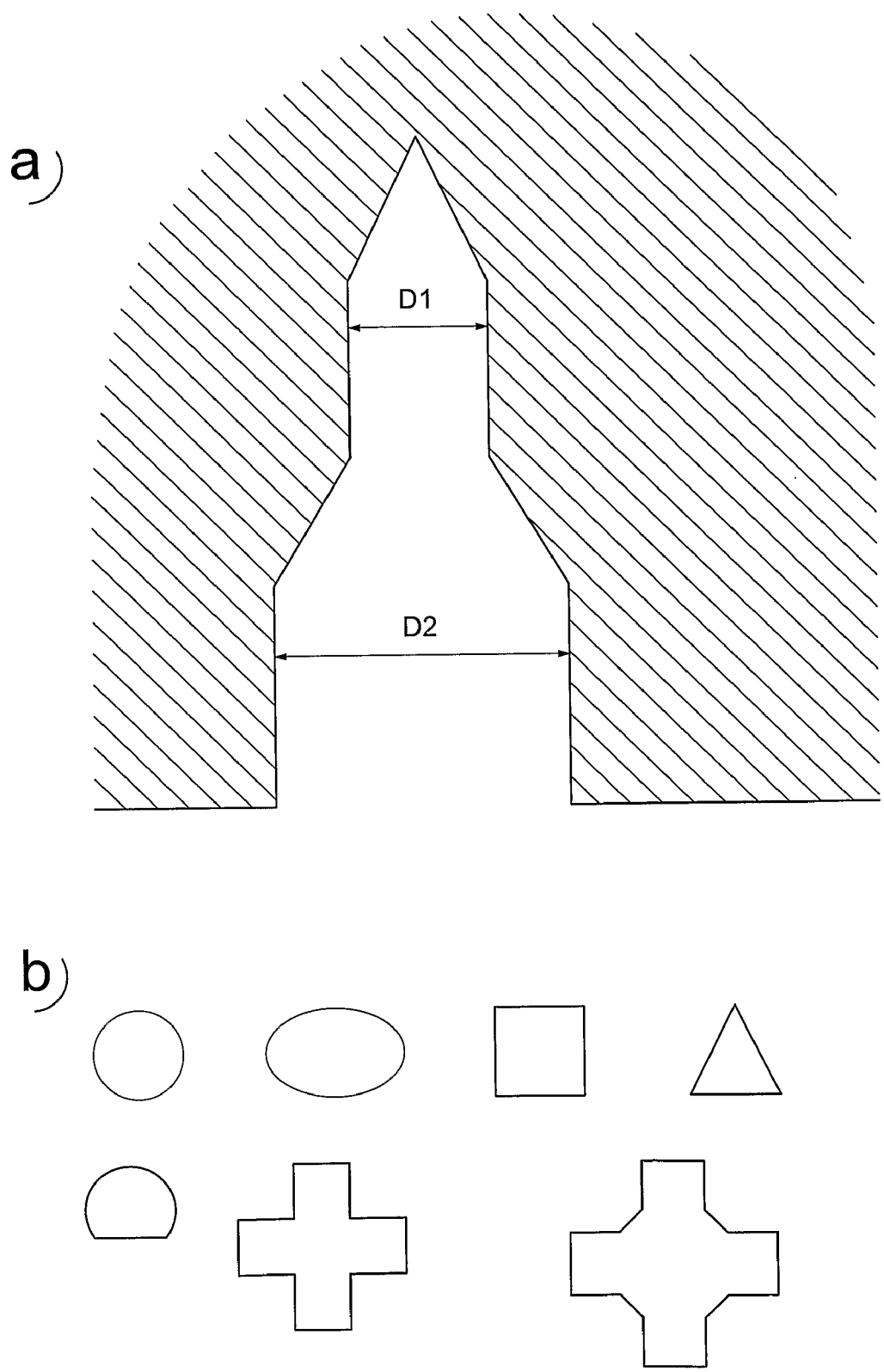
FIG. 1*a* is a schematic side view in cross-section of a negative mold usable in the invention.
FIG. 1*b* shows different possible cross-sectional shapes of the negative mold.

The following description will illustrate the method according to the invention, but the description shall not be taken as limiting on the scope of protection conferred by the appended claims.

The invention relates to a method for the replication of a micro-needle having side openings, using a polymer material, or any other moldable material. The method is general in the sense that it can be used for the replication of entire arrays of micro-needles, i.e. a number of micro-needles can be produced in parallel by the described method.

The method relates generally to making hollow micro-projections having side walls and at least one opening in a side wall, by a molding technique. The hollow micro-projections are defined by a first, negative mold defining the exterior shape of said micro-projections and a second, positive mold defining the hollow interior shape of said micro-projections.

In a first embodiment, the method of making hollow micro-projections having side walls and at least one opening in a side wall, accordingly comprises providing an essentially cylindrical negative mold defining the exterior shape of said micro-projections. An essentially cylindrical positive mold defining the hollow interior shape of said micro-projections is also provided. The positive mold is brought into said negative mold, such that at least one portion of a side wall of said positive mold comes close enough to, and preferably in contact with, at least one portion of said negative mold to define an area corresponding to the desired side opening. A desired structure is molded by filling the space between said positive and negative mold with a moldable material. Finally, the desired structure is demolded from the molds. Any (molded) material that may be present within the area defining the side opening is removed so as to form said opening.

In other words, the step of bringing the molds close to each other comprises displacing the positive mold in a lateral direction with respect to the negative mold, after the mold halves have been brought together, such that the portion defining the interior of the needle comes close to or in contact with one inner surface of the negative mold.

When the material is solidified enough to be self-supporting, the desired structure is de-molded from the molds.

In a second embodiment the method comprises injecting a moldable material into the space between the two molds, in a state where they have been brought together. The positive and negative molds each have an essentially cylindrical geometry. In the process of bringing the molds together, the mold halves are laterally off-set with respect to each other, such that the distance between an inner wall of the negative mold and the positive mold in said area, ranges from zero to a finite distance. Said distance is smaller than the largest distance between the walls of the molds, thereby defining a side opening in an area of a side wall of said negative mold, so as to provide an opening or at least a thinner material thickness in said side wall area compared to the remaining side walls.

If necessary, a step of removing residual material from said area defining the side opening to open it up to create an opening is performed.

Suitably the structure is subjected to a hardening procedure, before demolding the thus created molded structure from the molds.

If a hardening procedure, such as sintering, must be performed outside the mold, the method comprises demolding the thus created molded structure from the molds, before subjecting the structure to a hardening procedure.

The moldable material is suitably a polymer material, preferably selected from the group consisting of thermoplastic material, thermoset polymers, UV curing polymers, cross-linkable multi-component polymers.

In another embodiment, the moldable material is a ceramic or a metal powder, suitably mixed with a suitable binder.

Preferably, the step of removing material to open up the side opening comprises an etching process, such as a plasma etch, although other options are available to the skilled man without undue experimentation.

The product obtained by the process is a micro-projecting element, such as a needle, comprising a generally cylindrical, hollow body having a closed pointed tip, and at least one side opening extending along a side wall of said cylindrical body, made from a moldable material, preferably selected from polymers, ceramics or sintered metal.

In a further aspect there is provided a micro-array of a plurality of micro-projecting elements, or needles, projecting from a generally planar substrate surface.

Figure 2:
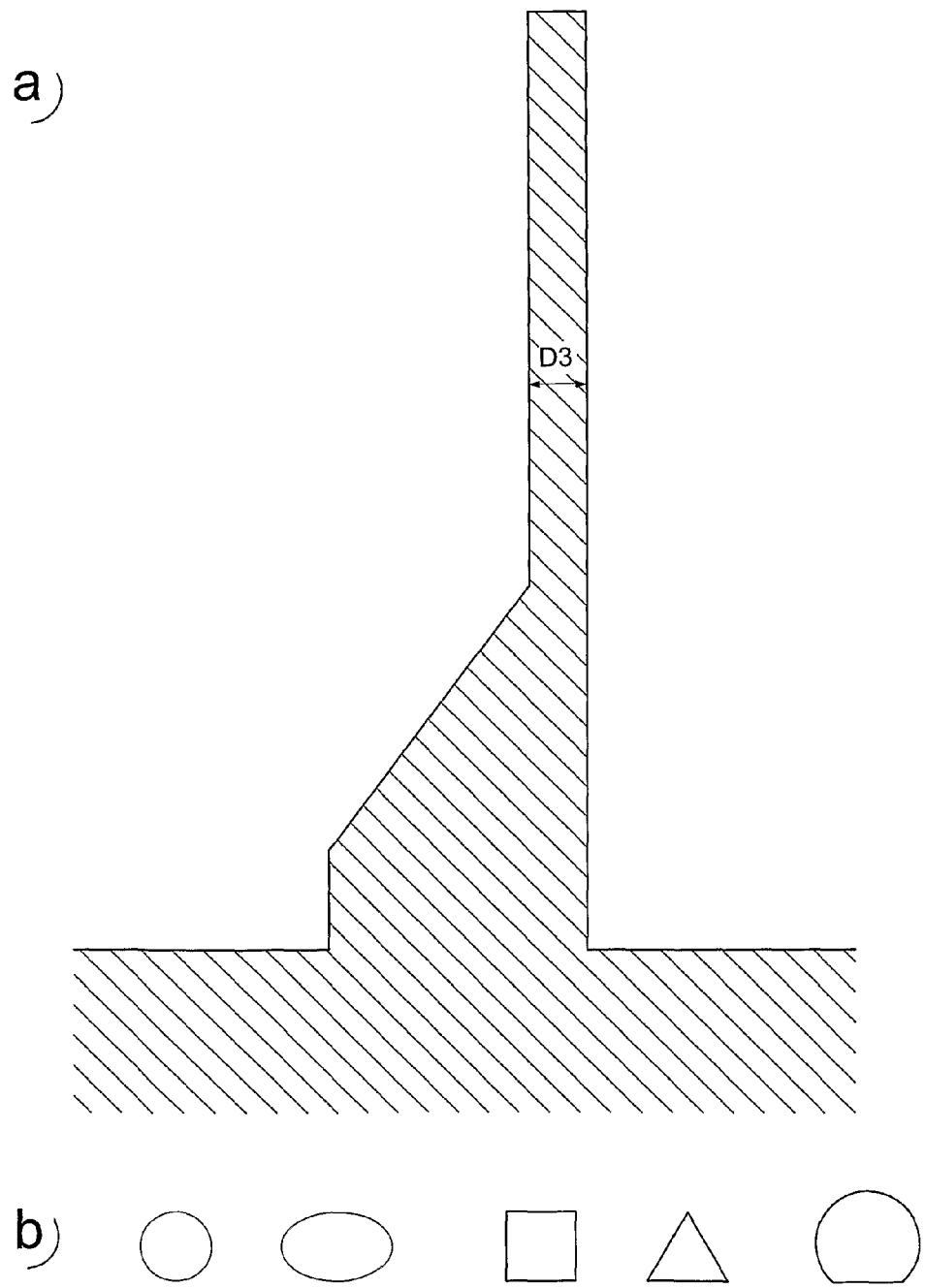
FIG. 2*a* is a schematic side view in cross-section of a positive mold usable in the invention.
FIG. 2*b* shows different possible cross-sectional shapes of the positive mold.

The method according to the invention requires two molds: 1) a negative mold, comprising a hole or depression in its surface, which defines the exterior shape of the needle, shown in FIG. 1a, and 2) a positive mold, which defines the inner lumen and the side opening of the needle, and shown in FIG. 2a.

The negative mold can be grown by employing a metal electroplating process, which is a methodology well known per se by the skilled man, using for example, a silicon master. A suitable metal is nickel, but other metals are possible too. The silicon master is made by silicon etch procedures which also are known per se and the skilled man would have no difficulty in finding a suitable way of making it. A procedure for making a master is disclosed in our pending patent application WO 03/015860, the disclosure of which is hereby incorporated herein in its entirety.

However, the master can be made in other materials than silicon or by using other processes than etching. For example it is possible to use an elastomer casting process, where the silicone master is coated with an elastomer material, e.g. silicone.

Instead of growing or casting a mold on a master, the mold may also be directly machined, e.g. by milling processes or by electro-erosion, in the substrate material to form the mold structure. A suitable material for the latter type of process is steel or other metals. Other materials that are possible to use encompass polymers (such as PMMA, although other polymer materials are possible too) and ceramics.

The negative mold in one embodiment exhibits the features shown in FIG. 1a. In particular, the mold is made from a cylindrical master which features a sharp tip and which features at least one distinct diameter, but preferably two distinct diameters D1 and D2.

The cross section of the master can be of any shape, but in particular it is circular, rectangular, elliptic, triangular or cross shaped. Non-limiting examples are shown in FIG. 1b, and practically any shape can be used to meet a specific requirement. Note that the cross section at D1 does not necessarily have to have the same geometry as the cross section at D2.

At present it is believed that a generally circular shape of the positive mold is preferable for most applications. However, it shall no be regarded as a limitation, since certain applications may well require other geometries for optimal performance.

The front side mold, made from the cylindrical master, and which comprises a number of depressions with a negative of the master, will be referred to as a negative mold below. This mold half will define the exterior shape of the micro-protrusion (needle) that is formed.

The back side mold, comprising a number of protruding elements or pins, will be referred to as a positive mold below. This mold half will define the interior shape of the micro-protrusion (needle) that is formed. It is made, for example, from a silicon master using similar or the same techniques as described above, or can be machined, using the same methods as described above, directly from the mold material. The positive mold exhibits the features shown in FIG. 2a. The mold consists of cylindrical (prismatic) structures, below referred to as pins. The pins have at least one diameter D3. The cross section of the pins may have any geometry, but in particular may be circular; elliptic; triangular; rectangular; or a circle segment (i.e. the area defined by a chord and the portion of a circle connecting to the chord), see FIG. 2b. The pins of the positive mold can have more than one particular cross section geometry, i.e. the geometry may vary along the length of the pins. However the geometry may not be varied such that the structure that has been made by molding, cannot be demolded from the molds.

Figure 3:
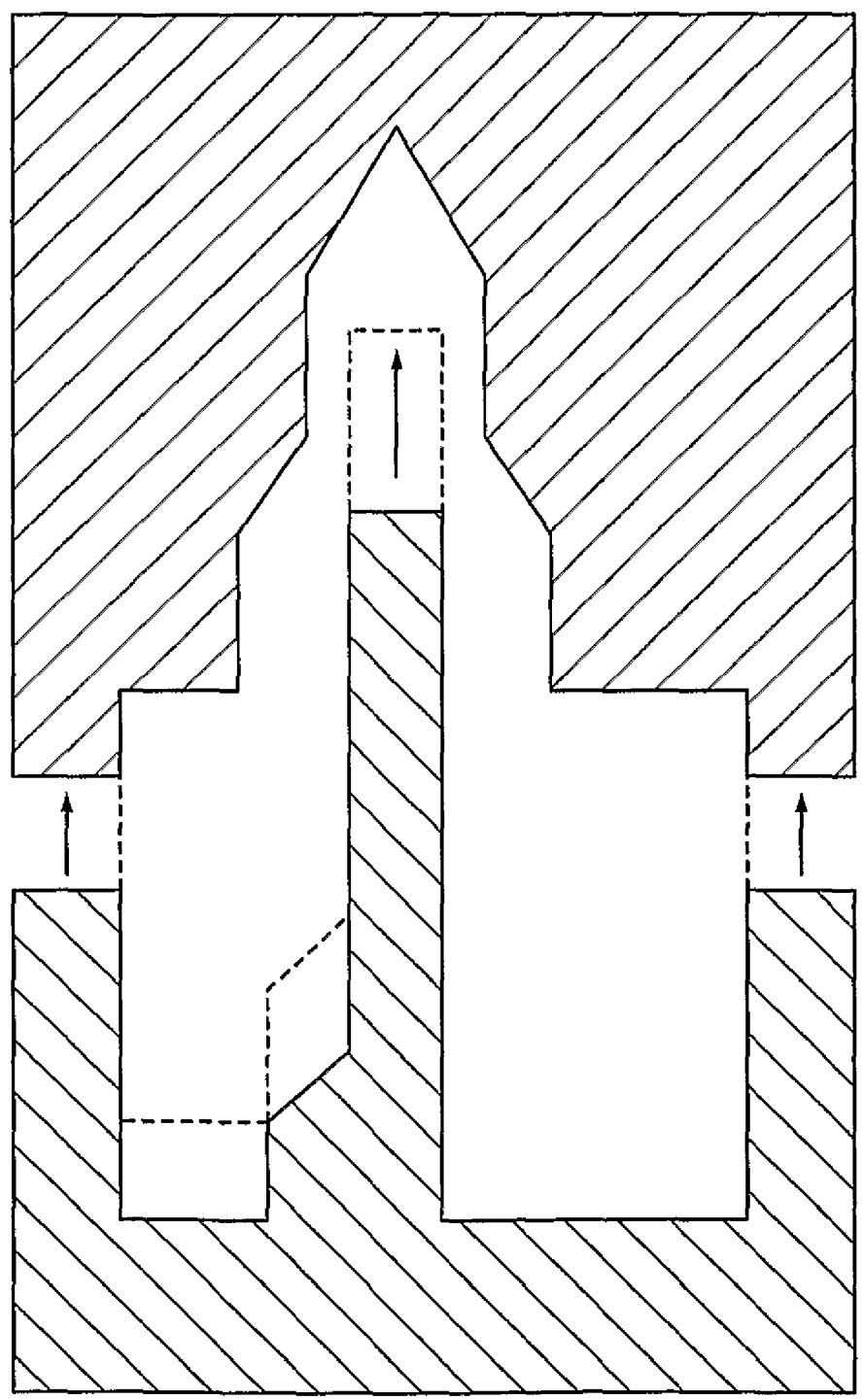
FIG. 3 shows alignment of the molds in the method according to the invention.

In a preferred embodiment, the replication process is performed in two steps. Namely, first the two molds are aligned and then joined, as shown in FIG. 3. At this stage, the pins do not touch the wall the negative mold. Thereafter, in a second step, by laterally moving the front and backside molds with respect to each other, the pins will come into contact with one wall of the negative mold. This is illustrated in FIG. 4.

Figure 4:
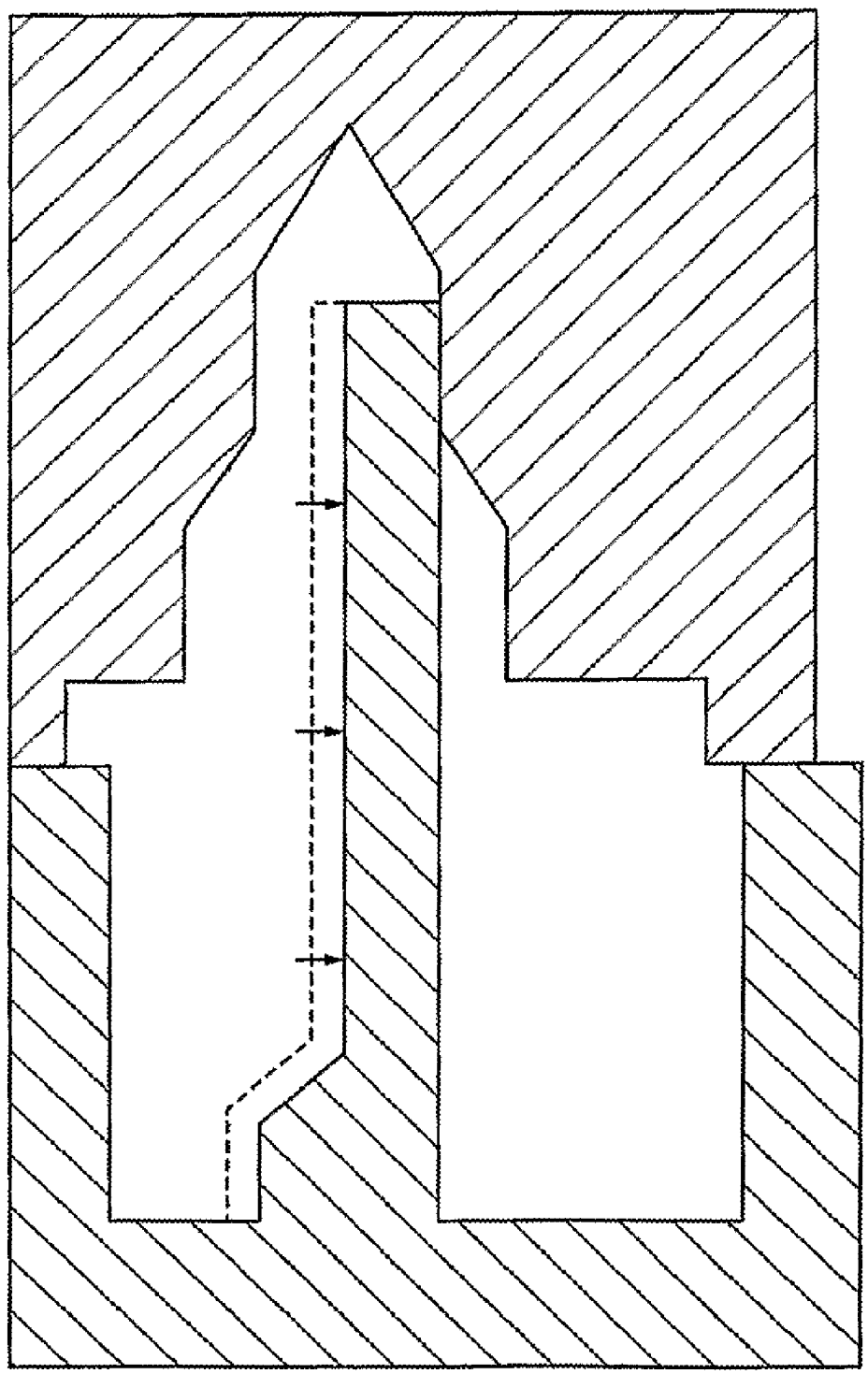
FIG. 4 shows one embodiment of the invention including the off-setting the molds relative to each other.
Figure 5:
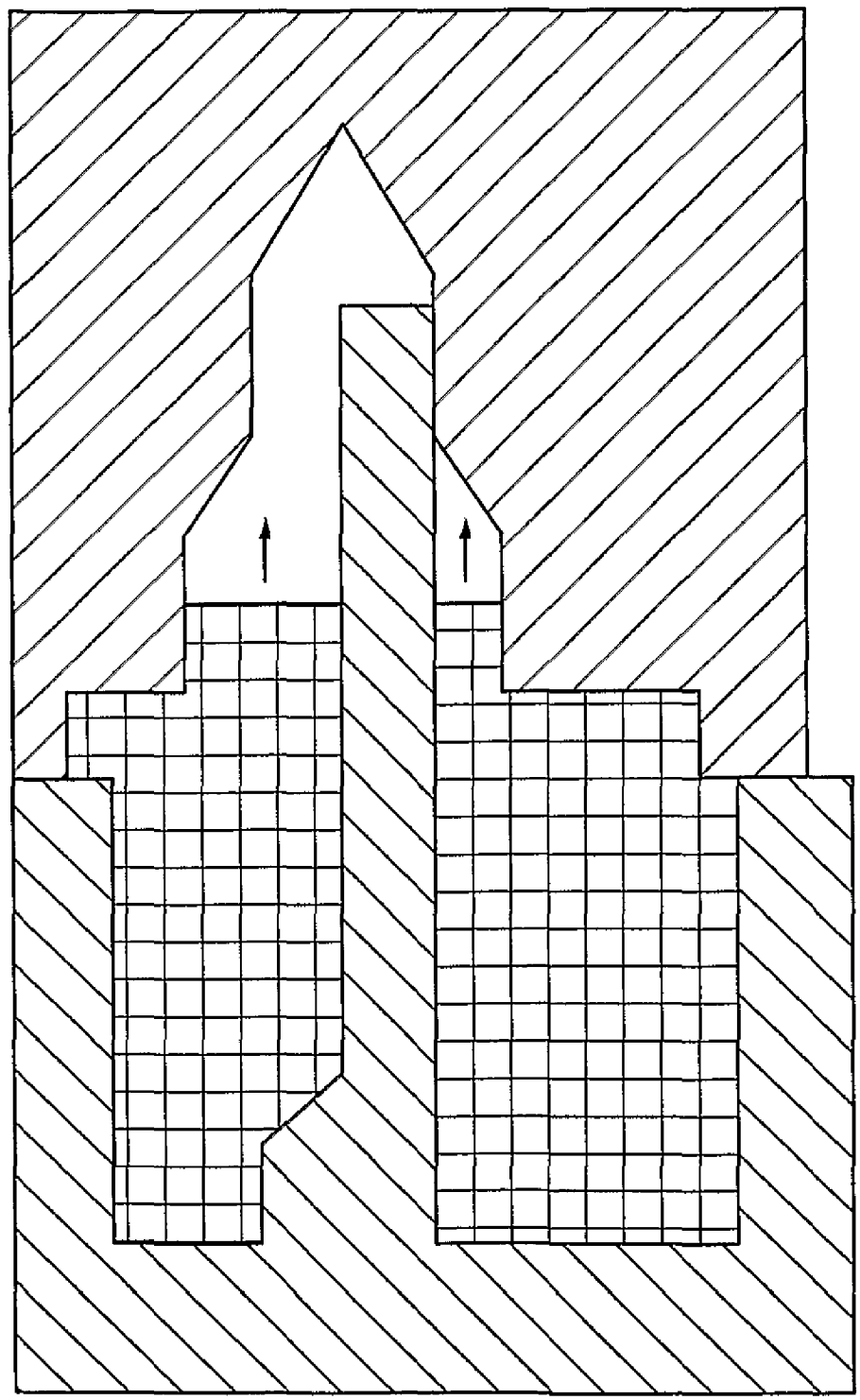
FIG. 5 shows filling of the mold with a moldable material.

When the molds have been fixed in the relative position disclosed in FIG. 4, a polymeric material is injected into the aligned mold. At the contact position between shaft mold and pin and depending on the contact pressure, the polymer will either form a thin membrane (because the polymer material will penetrate in between the two molds) or the side opening in the needle is created directly because the polymer is not able to penetrate in between the two molds. This is illustrated in FIG. 5.

Various different alternatives will be available for bringing the pins in contact with the wall of the positive mold.

Consider a case where both molds are cylindrically shaped. Here the contact will be defined essentially by a line where the two different diameters touch. Thereby, the molding material when injected will fill up the space inside the molds such that there will be provided an extremely narrow slit, or at least a very narrow portion with very thin material thickness (the latter occurs if the material penetrates in between the mold halves, as suggested above).

Subjecting the demolded structure for a directed plasma etch will then open up a side opening in the protrusion (needle).

Another option is to provide the pin with a surface portion that exactly conforms to the inner wall of the negative mold. In such a case, and where the negative mold is circular, the pins would be provided with a surface portion having exactly the same curvature as the wall of the negative mold. This will create a plane of contact, rather than a line of contact between the mold halves. This will increase the probability of a side opening to form directly during the molding process, and if at all necessary, a plasma etch can be performed very quickly just to remove any excess material "masking" off the edges of the side opening that was created.

If the negative mold has flat walls, i.e. having no curvature, the pins would also be provided with a flat portion, so as to form a plane of contact, similar to the above situation.

The skilled man will be able to conceive other possible combinations of contact lines and/or contact planes, to meet any requirements on the shape or design of the side opening.

For example one could envisage having a pin with a small radius of curvature at the top and radius of curvature further down that matches that of the negative mold. This would create a side opening having a narrow top and a wider bottom portion.

Figure 6:
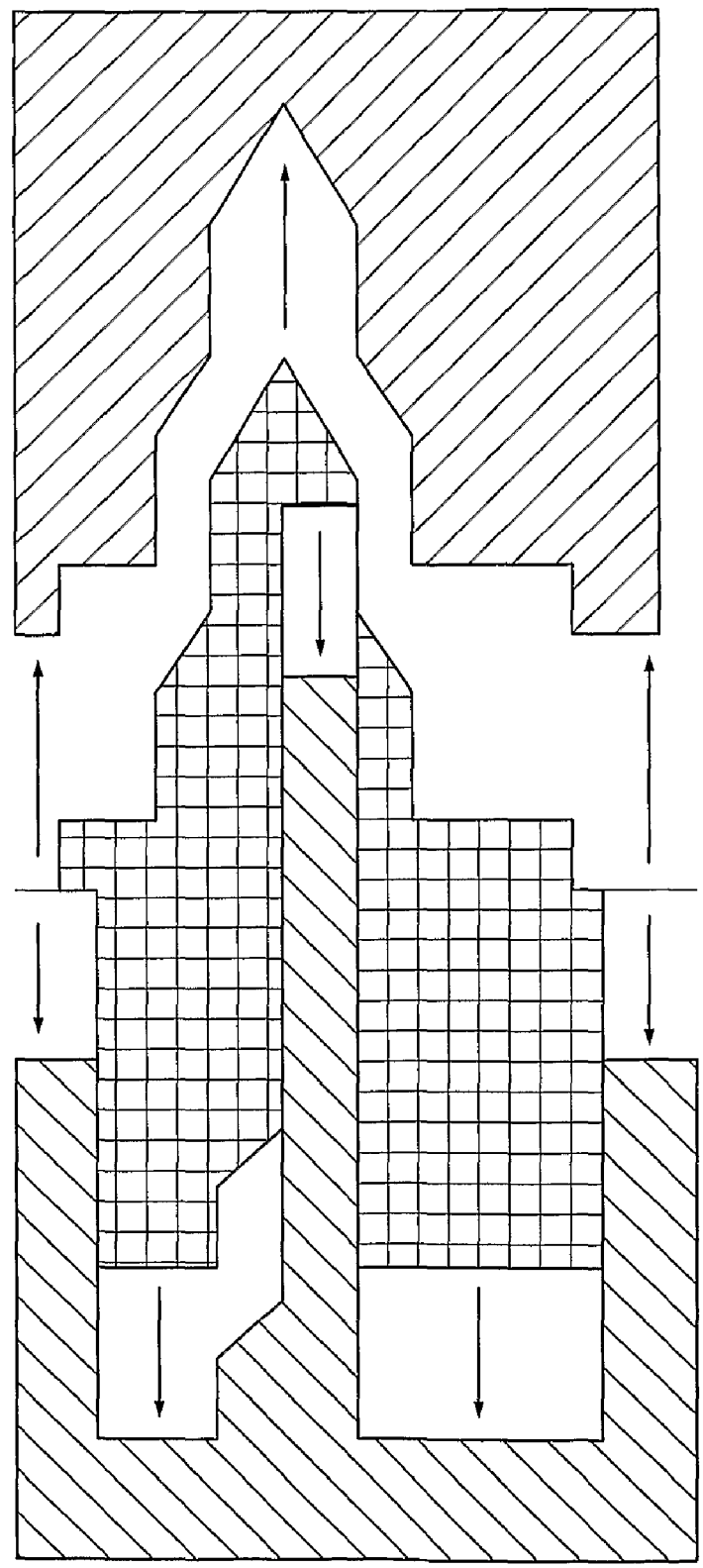
FIG. 6 shows demolding of a molded structure in the form of a hollow micro-projection having a side opening.

The finished molded structure (micro-needle) is then demolded by retracting the two molds, as can be seen in FIG. 6.

Although it is at present regarded as a preferred embodiment to perform the method as shown in FIGS. 3-6, i.e. by performing an lateral off-set of the molds with respect to each other in order to bring about the contact needed to create the side opening, it is also possible to achieve the same result in a second way.

Figure 8:
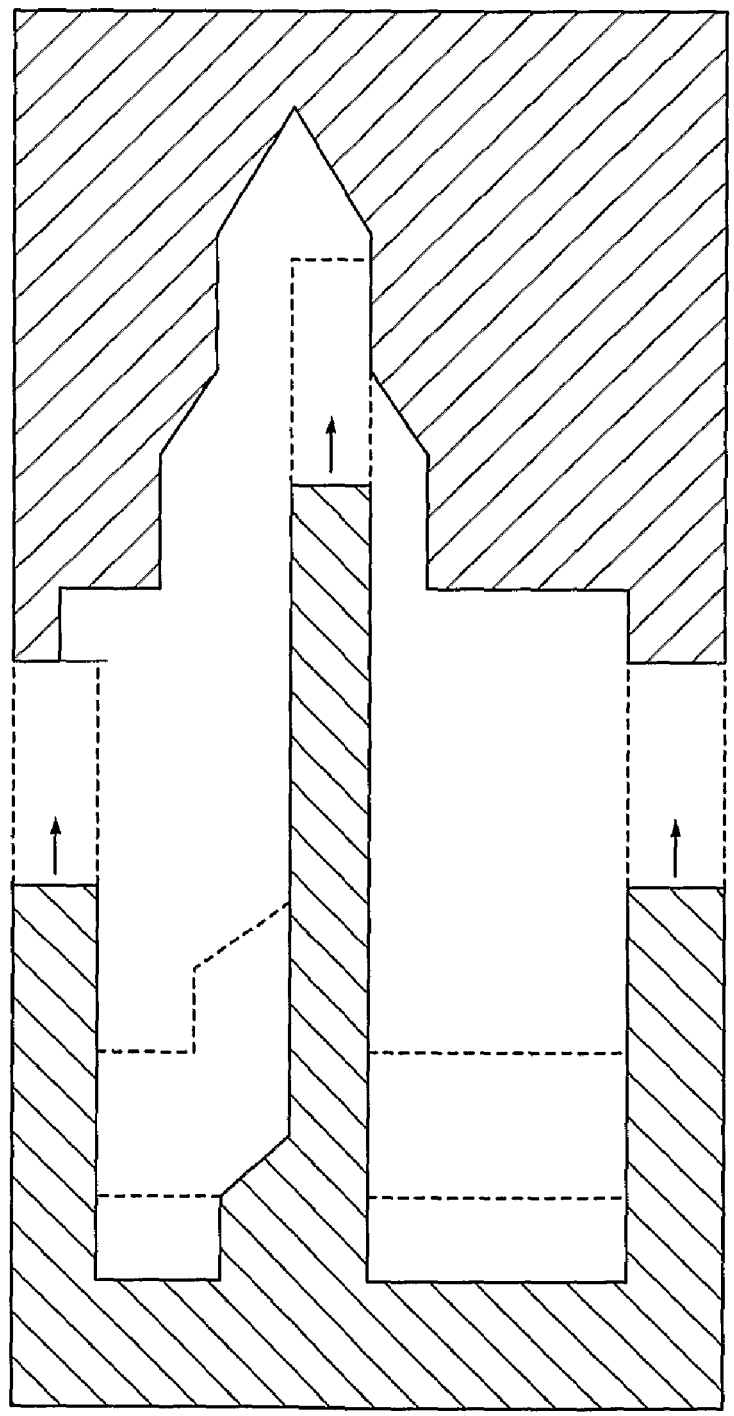
FIG. 8 illustrates a second embodiment of the method according to the invention.

Namely, it is possible to align the molds directly such that the contact between the molds occur in the alignment action, as shown schematically in FIG. 8. Thereby, the positive mold is simply aligned with respect to the positive mold such that the location of the protruding pin is already in the lateral position required for a contact between the pin and the negative mold, when the molds are brought together, as indicated by the arrows.

Figure 7:
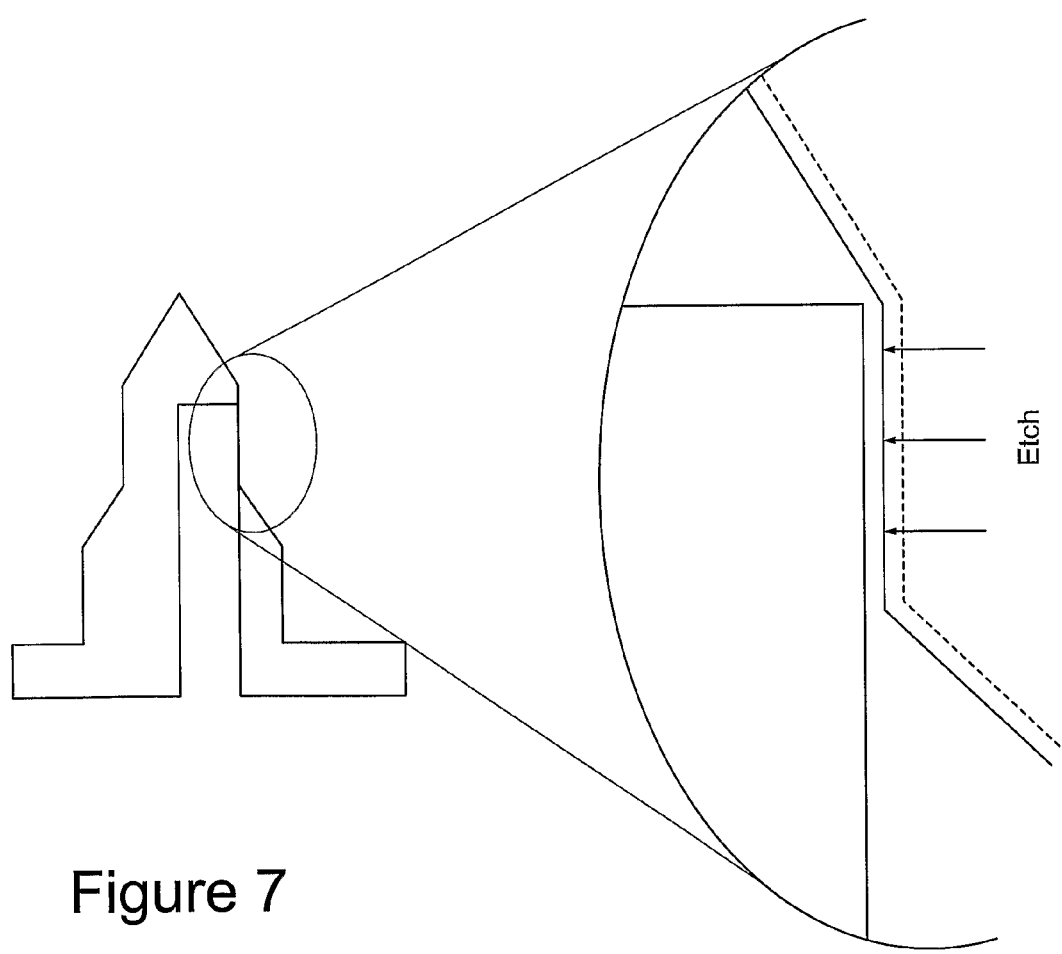
FIG. 7 illustrates the optional step of plasma etching in the event that there remains material in the area defining the side opening.

In the event that there is a thin membrane of polymer material left at the position of the side openings to be (e.g. because the contact pressure between pin and shaft mold is too small, such that polymer material has been able to penetrate in between the positive and the negative mold at the point of contact), the needle may be placed in a plasma etcher to remove the remaining polymeric membrane. FIG. 7 illustrates the removal of membrane by exposure to a plasma etch.

The replication process can be performed with a number of different materials, polymers being the preferred material type. As a polymeric material, for example thermoset polymers, thermoplastics, UV curing polymers, or cross linked multiple component polymers can be used. The micro-needles may also be replicated in ceramics, or metal powder, suitably mixed with an appropriate binder.

The micro-projections according to the present invention can have many applications, some of which are found in the medical field. Thus, for reducing the traumatic experience in injecting medicaments through the skin, the micro-projections are very suitable. Namely, the pain experienced by a patient will be substantially reduced if an array of several hundred or thousand needles are used instead of one coarse needle.

Although the invention has been described with reference to specific embodiments, the skilled man will find numerous other variations and modifications, all of which are within the scope of the appended claims.

The invention claimed is:

1. A method of making hollow micro-projections having side walls and at least one opening in a side wall, comprising providing an essentially cylindrical negative mold defining the exterior shape of said micro-projections; providing an essentially cylindrical positive mold defining the hollow interior shape of said micro-projections; bringing said positive mold into said negative mold, and off-setting the mold halves laterally with respect to each other, such that the distance between an inner wall of the negative mold and the positive mold in said area, ranges from zero to a finite distance which is smaller than the largest distance between the walls of the molds, thereby defining a side opening in an area of a side wall of said negative mold, so as to provide an opening or at least a thinner material thickness in said side wall area compared to the remaining side walls, such that at least one portion of a side wall of said positive mold comes close enough to, and preferably in contact with, at least one portion of said negative mold to define an area corresponding to the desired side opening; molding a desired structure by filling the space between said positive and negative mold with a moldable material; demolding the desired structure from the molds; and s"^ removing any molded material that may be present within the area defining the side opening so as to form said opening.

2. The method as claimed in claim 1, comprising subjecting the structure to a hardening procedure, before demolding the thus created molded structure from the molds.

3. The method as claimed in claim 2, wherein the moldable material is a polymer material.

4. The method as claimed in claim 3, wherein the polymer is selected from the group consisting of thermoplastic material, thermoset polymers, UV curing polymers, cross-linkable multi-component polymers.

5. The method as claimed in claim 1, comprising demolding the thus created molded structure from the molds, before subjecting the structure to a hardening procedure.

6. The method as claimed in claim 5, wherein the moldable material is a ceramic or a metal powder.

7. The method as claimed in claim 6, wherein the moldable material is mixed with a suitable binder.

8. The method as claimed in claim 7, wherein the molded structure is sintered after demolding, but before the step of removing any material in the area defining the side opening.

9. The method as claimed in claim 1, wherein the step of removing material comprises an etching process.

10. The method as claimed in claim 9, wherein the etching process comprises plasma etch.

11. The method as claimed in claim 1, wherein the step of bringing the molds close to each other comprises displacing the positive mold in a lateral direction with respect to the negative mold, after the mold halves have been brought together, such that the portion defining the interior of the needle comes close to or in contact with one inner surface of the negative mold.

* * * * *